(12) United States Patent
Schultz

(10) Patent No.: US 6,755,815 B2
(45) Date of Patent: Jun. 29, 2004

(54) SURGICAL INSTRUMENTS FOR MINIMALLY INVASIVE SURGICAL PROCEDURES

(76) Inventor: Leonard S. Schultz, 11036 Boone Cir. South, Bloomington, MN (US) 55438

( * ) Notice: Subject to any disclaimer, the term of this patent is extended or adjusted under 35 U.S.C. 154(b) by 269 days.

(21) Appl. No.: 09/891,743

(22) Filed: Jun. 26, 2001

(65) Prior Publication Data

US 2001/0034535 A1 Oct. 25, 2001

Related U.S. Application Data

(60) Continuation of application No. 09/601,288, filed on Jul. 28, 2000, now Pat. No. 6,520,953, which is a division of application No. 09/308,700, filed on May 21, 1999, now Pat. No. 6,096,026.
(60) Provisional application No. 60/059,440, filed on Sep. 22, 1997.

(30) Foreign Application Priority Data

Sep. 22, 1998 (WO) .............................. PCT/US98/19751

(51) Int. Cl.[7] .............................................. A61B 17/04
(52) U.S. Cl. ........................................ 606/1; 606/190
(58) Field of Search ................................ 206/339, 340; 433/3; 600/240

(56) References Cited

U.S. PATENT DOCUMENTS

| | | | |
|---|---|---|---|
| 3,768,477 A | | 10/1973 | Anders et al. |
| 3,943,592 A | | 3/1976 | Bhaskar et al. |
| 4,688,560 A | | 8/1987 | Schultz |
| 5,144,942 A | * | 9/1992 | Decarie et al. ................ 606/1 |
| 5,261,817 A | | 11/1993 | Nack |
| 5,282,816 A | * | 2/1994 | Miller et al. ................ 606/167 |
| 5,382,256 A | | 1/1995 | del Castillo |
| 5,400,768 A | * | 3/1995 | McNamara et al. ........ 600/104 |
| 5,423,856 A | | 6/1995 | Green |
| 5,489,287 A | | 2/1996 | Green et al. |
| 5,725,479 A | * | 3/1998 | Knight et al. ............... 600/210 |
| 5,846,195 A | | 12/1998 | Reis |
| 6,096,026 A | | 8/2000 | Schultz |

* cited by examiner

Primary Examiner—Gary Jackson
(74) Attorney, Agent, or Firm—Dorsey & Whitney LLP

(57) ABSTRACT

The present invention provides a group or kit of surgical instruments for use in minimally invasive surgical procedures. In one embodiment, the invention is an instrument with a generally central longitudinal axis and a generally toroidal surface generally transverse to the axis, wherein the convex portion of the surface does not extend beyond a line parallel with the longitudinal axis along an outer diameter of the instrument, and the surface has a continuous edge having a first end at a shoulder and a second end at the shoulder and spaced from the first end; in another embodiment, the instrument has a working end with a generally longitudinal axis, the working end defined by a generally curved surface along the longitudinal axis, wherein the curved surface has a concave portion and a convex portion, and wherein the working end has a generally flat tip; in another embodiment, the surgical instrument includes a working end having a generally central longitudinal axis and a surface generally transverse to the axis, wherein the surface is generally spatulate and oval, and wherein the surface is set at a selected angle relative to the axis; and in yet another embodiment, the surgical instrument comprises a straight pin for being placed into bone, the pin having a sharp tip, a number of spaced steps generally adjacent to the tip, marks adjacent to the steps, and an end opposite the tip for hammering.

1 Claim, 8 Drawing Sheets

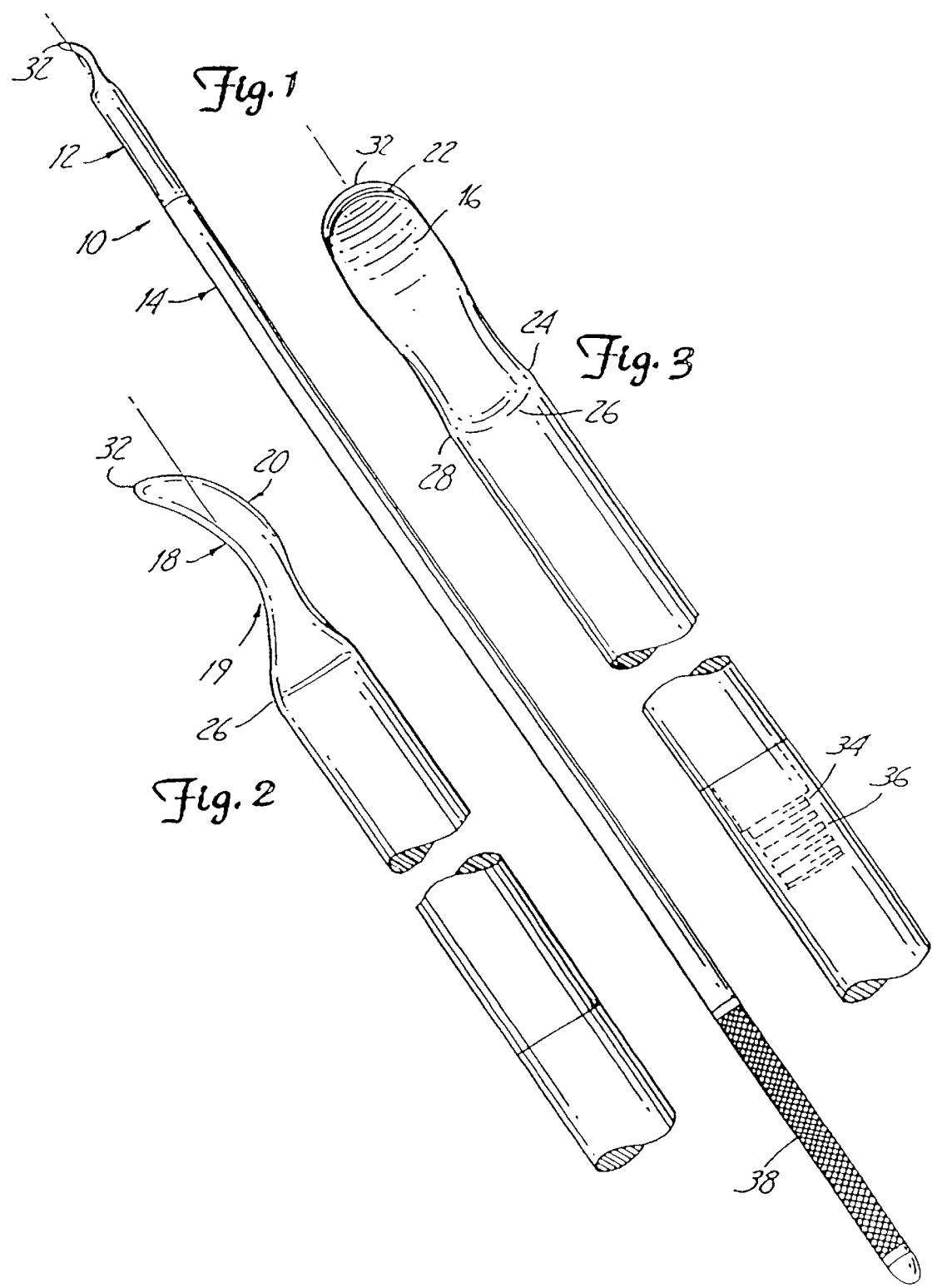

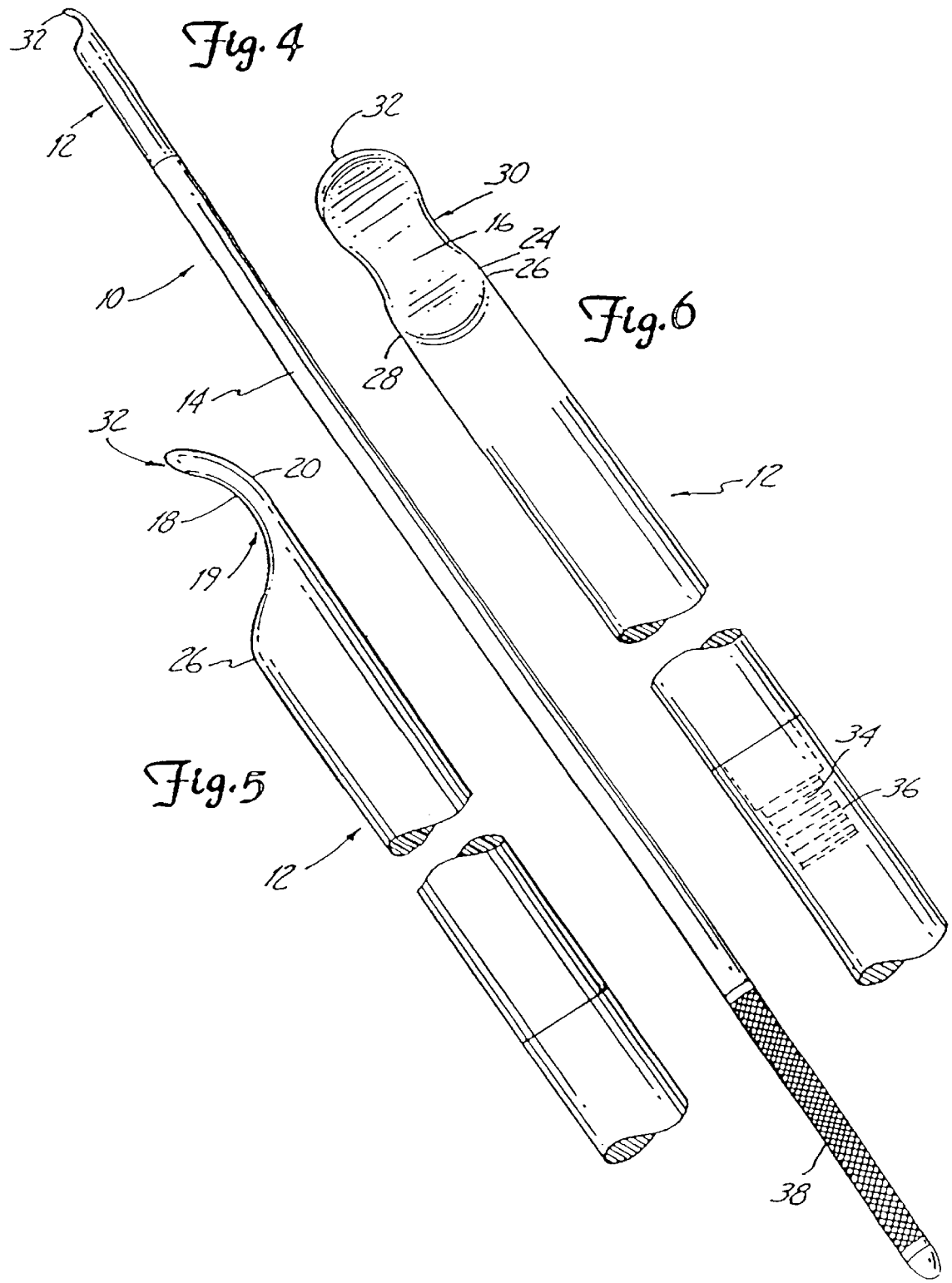

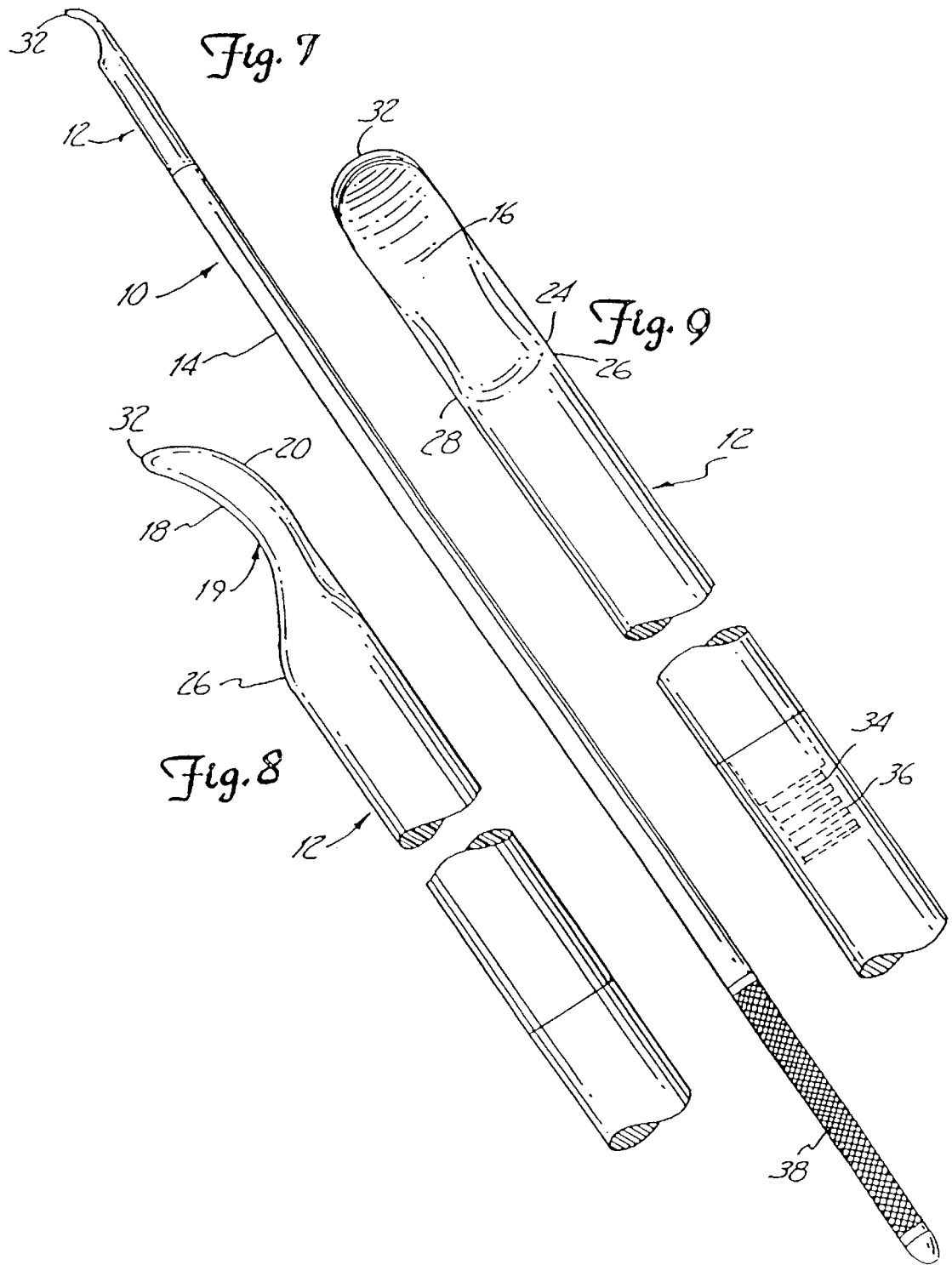

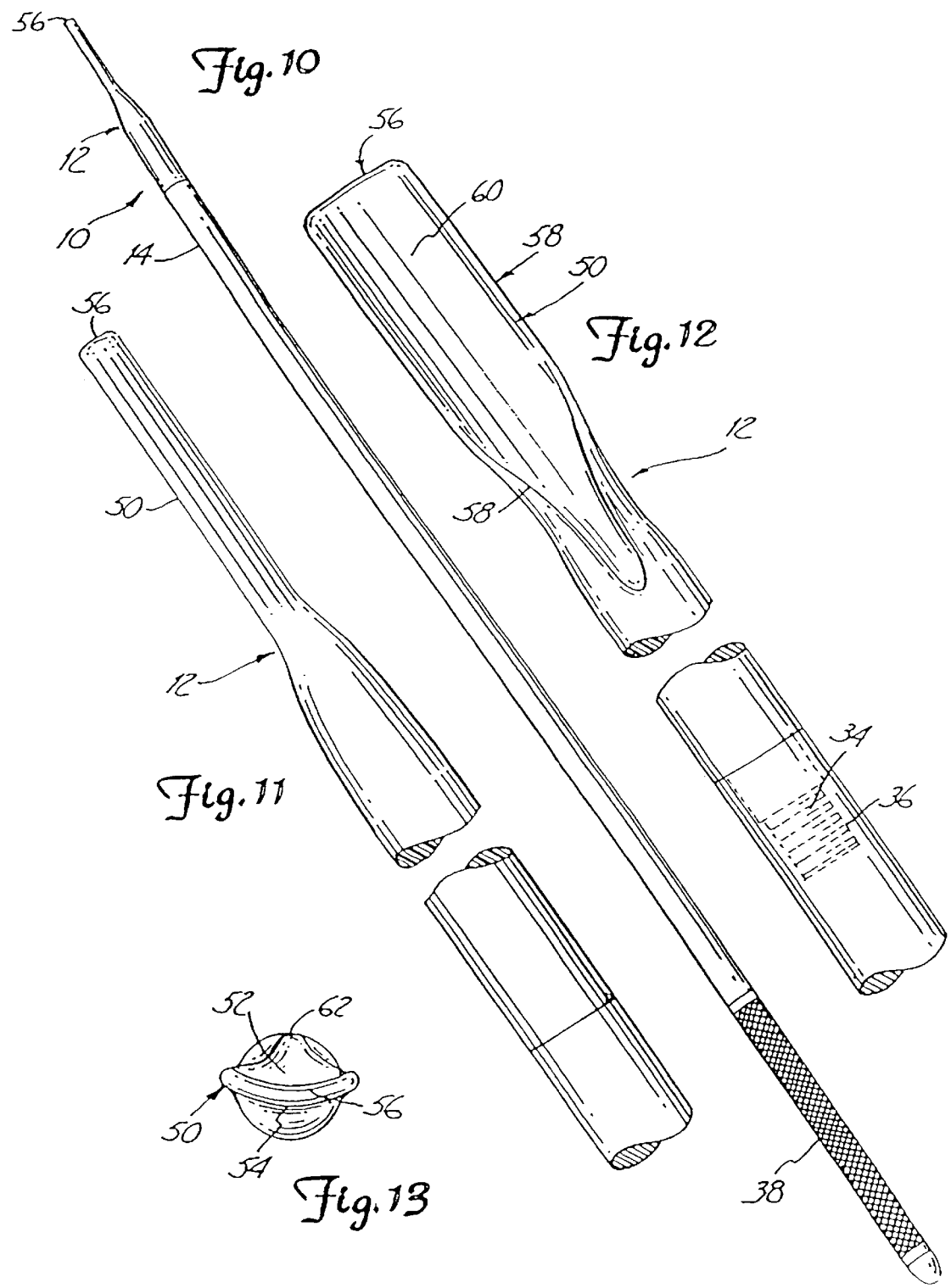

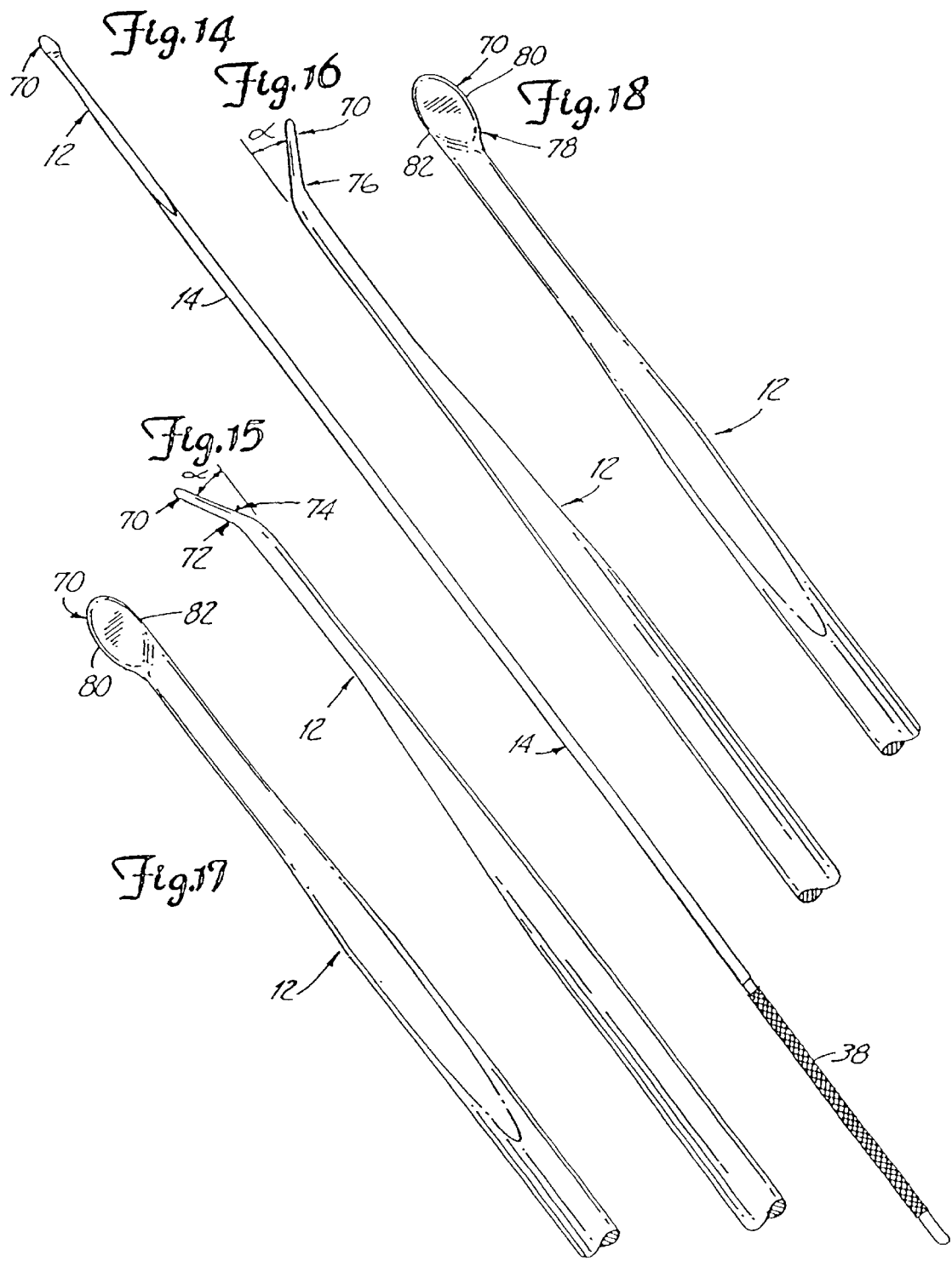

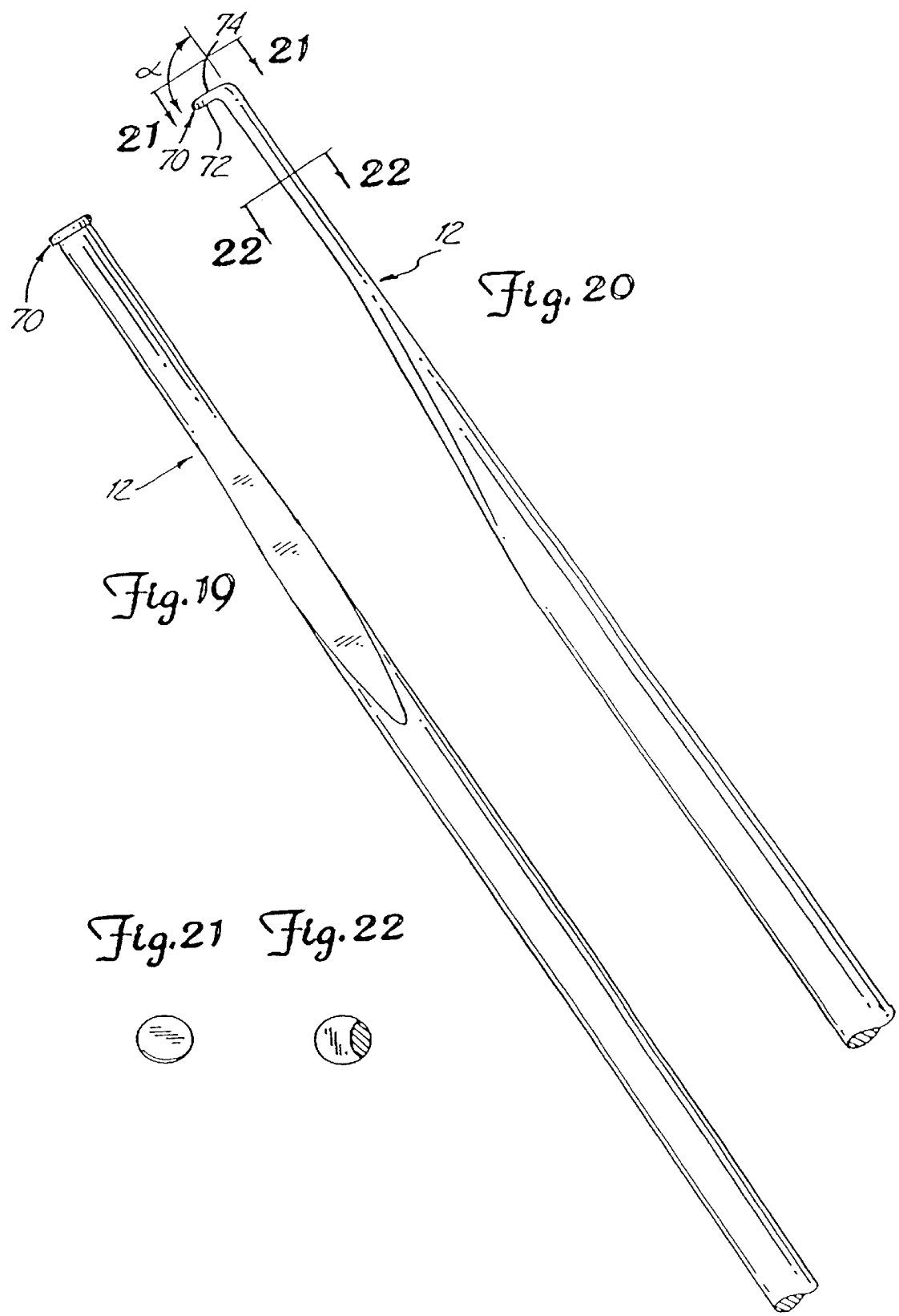

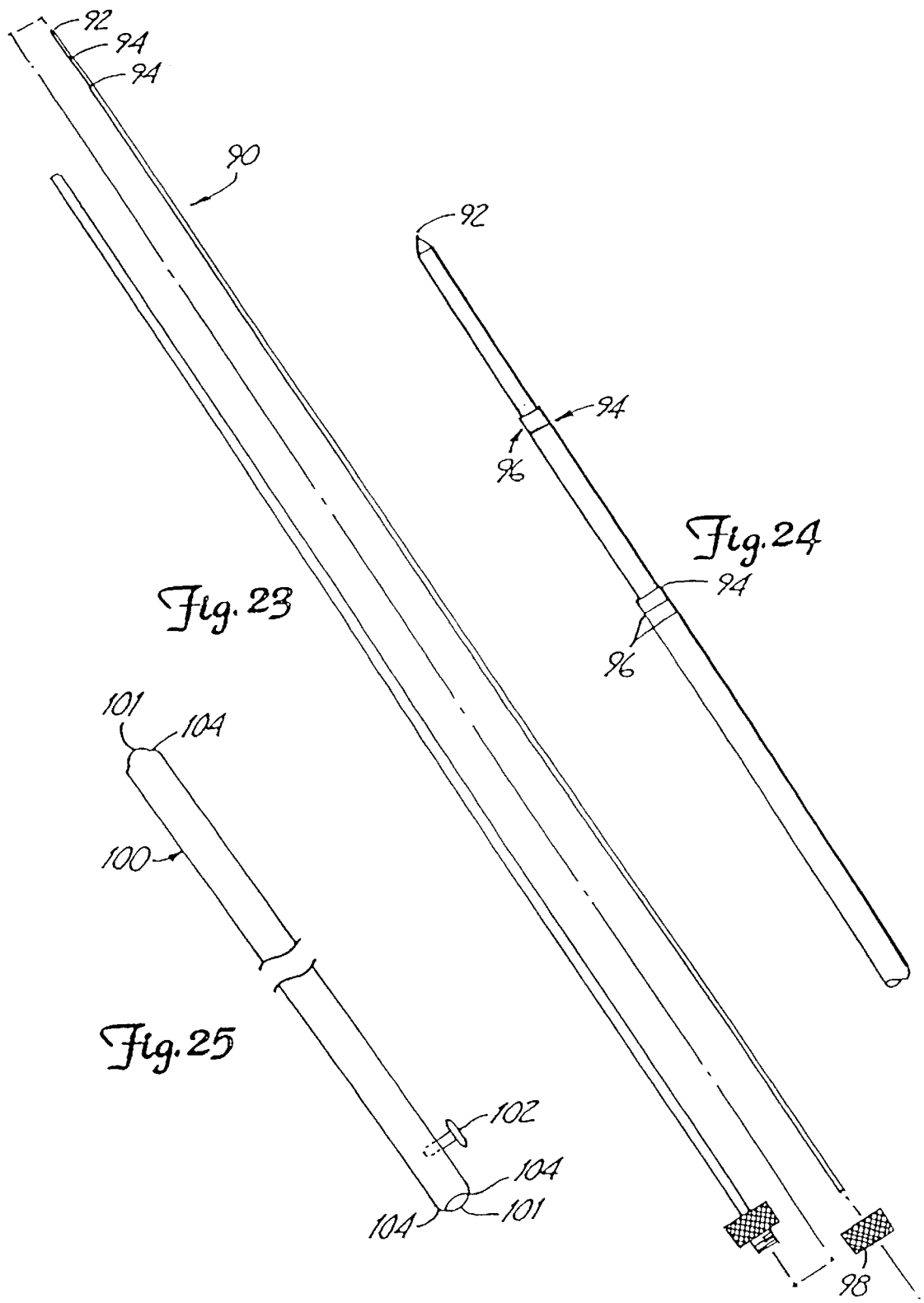

SURGICAL INSTRUMENTS FOR MINIMALLY INVASIVE SURGICAL PROCEDURES

RELATED APPLICATIONS

This application is a continuation of U.S. patent application Ser. No. 09/601,288, filed Jul. 28, 2000 U.S. Pat. No. 6,520,953, which was a divisional of U.S. patent application Ser. No. 09/308,700, filed May 21, 1999, now U.S. Pat. No. 6,096,026, issued Aug. 1, 2000, which claims the priority of PCT application PCT/US98/19751, filed Sep. 22, 1998, and of U.S. provisional patent application serial No. 60/059,440, filed Sep. 22, 1997, all of which are incorporated herein by reference.

BACKGROUND OF THE INVENTION

1. Field of the Invention

This invention relates to instruments for use in medical procedures. More particularly, this invention relates to a set of surgical instruments substantially for dissection and retraction in minimally invasive surgical procedures such as laparoscopy and mini-laparotomy.

2. Background Information

Surgical tools are commonly used in minimally invasive surgical procedures, such as mini-laparotomy, laparoscopic or thoracoscopic surgery, to provide mechanical handling of tissue. For example, during surgery on or adjacent to the spine the surgeon should have clear access to the desired intervertebral discs or vertebrae for purposes of discetomy, vertebrectomy, spinal decompression, or placement of fusion disc devices, prosthetics, or other hardware. Surgical tools may be used for dissection and/or retraction of blood vessels or other bodily tissues to provide clear access to the desired area. In some spinal procedures, the surgical entry point is on the abdominal side of the patient's body, so the tools must provide clearance so that the entire diameter of the abdominal cavity may be traversed for performance of the surgical procedure.

In some minimally invasive surgical procedures, such as laparoscopic or thoracoscopic procedures, one or more trocars typically penetrate and/or are maintained or mounted in the wall of the body cavity to provide access for the surgical tools during the procedure. The trocars may form or act as ports into the body cavity for insertion and manipulation of surgical instruments. Some surgical instruments, particularly those with sharp tips or edges, are inserted and moved to a desired working location in the body in hollow tubes or sheaths to reduce the risk of harming other blood vessels or organs during traversal of the body. A video camera may be mounted on a laparoscope which is passed through a trocar port for visualization of the procedures in the body cavity on a monitor. Alternatively, an X-ray or other visualization system may be used to view the procedure, including the position of instruments relative to the surgical site, on a suitable monitor.

Generally it is desirable to reduce the number of trocar ports used during a surgical procedure to reduce trauma to the patient. For this reason, a plurality of surgical tools, including tools dedicated to a specific function, adapted to be inserted through a trocar are preferred so that blood vessels, tissue, and the area of the surgical procedure may be manipulated through a small number of trocar ports or through a mini-laparotomy incision.

A variety of tools, such as retractors, forceps, graspers, suture needles, and pins, currently exist and may be available for use during abdominal or thoracic procedures. Such tools, however, have certain deficiencies when minimally invasive access methods are used. One problem with available surgical tools is that they are not properly shaped for optimal harmless manipulation of blood vessels and other bodily tissue during laparoscopic or thoracoscopic procedures. Another problem with some surgical tools which might be appropriately shaped is that they do not fit through the tubes or trocars, so it can be difficult to traverse the body to reach the desired working location. The typical trocar is approximately 11 to 12 or less millimeters in diameter, and the hollow tubes therein are of approximately the same diameter. Some surgical tools have working ends of greater than 12 millimeters in length, and it would be difficult or impossible to insert these tools through typical trocars and tubes.

A need exists for surgical tools and methods which reduce potential trauma associated with surgery, including minimally invasive surgical procedures, and which aid the surgeon in manipulating blood vessels and tissue during surgical procedures. More specifically, a need exists for surgical tools for dissection and retraction that are shaped to allow a surgeon to manipulate blood vessels and other bodily tissue without harming the patient. The tools should also be properly shaped to perform specific functions or procedures conveniently and with minimal risk to the patient, yet they should be usable through typical trocars, ports or short incisions (e.g., incisions of the type used in mini-laparotomy).

SUMMARY OF THE INVENTION

The present invention provides instruments for use in surgical procedures. In one embodiment, the instruments of the present invention comprise a kit of instruments well-suited for use in minimally invasive surgical procedures, particularly such procedures involving or conducted near the spine. The kit includes at least one or more of the retractors described herein, one or more of the dissectors described herein and one or more of the pins described herein. It is anticipated that the kit would be available to surgeons through, for example, typical hospital or clinic supply arrangements, in the form of a sterilized prewrapped package of one or more of the instruments or selected embodiments of the instruments.

Each of the instruments comprising the kit is an embodiment of the present invention. One embodiment, the retractor(s), comprises a working end having a generally central longitudinal axis and a surface generally transverse to the axis, the surface being defined by a generally toroidal shape having a concave portion and a convex portion, the concave portion having a selected degree of openness, wherein the convex portion of the surface does not extend beyond a line parallel with the longitudinal axis along an outer diameter of the working end adjacent to the surface, and the surface has a continuous edge having a first end at a shoulder and a second end at the shoulder and spaced from the first end. This embodiment of the invention may further comprise a shaft coupled to the working end for handling the surgical instrument. The working end and shaft may be unitary (i.e., formed as a single piece), they may be permanently coupled or connected, or they may be separably joined.

In another embodiment, the retractor comprises a working end having a generally longitudinal axis, the working end being defined by a generally curved surface along the longitudinal axis, wherein the curved surface has a concave portion and a convex portion, and wherein the working end has a generally flat tip. Again, the working end may be formed as one piece with a shaft or handle, it may be permanently joined to a shaft, or it may be separably joined to a shaft.

Another embodiment, of the invention, the dissector(s), comprises a working end having a generally central longitudinal axis and a surface generally transverse to the axis, wherein the surface is generally spatulate and oval, and wherein the surface is set at a selected angle relative to the axis. In this embodiment, the surface may also be offset in reference to a shaft.

Another embodiment of the invention, the pin(s), comprises a straight pin for being placed or driven into bone, the pin having a sharp tip and a number of steps generally adjacent to the tip, as well as circular markings or etchings adjacent to each step separated at a 1 cm distance. Along the length of the pin, from the tip, the pin increases generally incrementally in diameter with each step, and has a first end opposite the sharp tip for hammering. In this embodiment, the invention may further comprise a hollow guide tube for removably receiving the pin as the pin is moved to the site of use, the pin being longer in length than the guide tube.

An advantage of the instruments of the present invention, particularly in kit form, is that they facilitate performing minimally invasive surgical procedures, particularly spinal procedures, wherein each instrument is well adapted for a particular function or manipulation of a particular tissue.

For example, the retractors are well suited for manipulation of tissues, for example, tissue adjacent or immediately adjacent to the spine, the common iliac artery and vein, segmental vessels or the cystic duct. The dissectors are well suited for manipulation tissues such as the mid-sacral and segmental blood vessels or the cystic, and the pins may be driven into bone, including vertebrae, to support or hold tissue(s) in a desired position during a surgical procedure.

Another advantage of the instruments of the present invention, particularly the retractors, is that they include a working end at least a portion of which is radiolucent, i.e., permeable to radiation, whereby a surgeon may have an improved visualization of other devices in use during a procedure and examined or displayed on an imaging system.

Another advantage of the instruments of the present invention, particularly the retractors and dissectors, is that they have smooth continuous edges, smooth working surfaces, and smoothly rounded edges and tips to reduce potential trauma to delicate tissue.

Other features and advantages of the surgical instruments of the present invention will become more fully apparent and understood with reference to the following description and drawings, and the appended claims.

DESCRIPTION OF THE DRAWINGS

FIG. 1 is a side view of one embodiment of the surgical instrument in its entirety;

FIG. 2 is a side view of the working end of the embodiment of FIG. 1;

FIG. 3 is a top view of the working end of the embodiment of FIG. 1;

FIG. 4 is a side view of another embodiment of the surgical instrument in its entirety;

FIG. 5 is a side view of the working end of the embodiment of FIG. 4;

FIG. 6 is a top view of the working end of the embodiment of FIG. 4;

FIG. 7 is a side view of another embodiment of the surgical instrument in its entirety;

FIG. 8 is a side view of the working end of the embodiment of FIG. 7;

FIG. 9 is a top view of the working end of the embodiment of FIG. 7;

FIG. 10 is a side view of another embodiment of the surgical instrument in its entirety;

FIG. 11 is a side view of the working end of the embodiment of FIG. 10;

FIG. 12 is a top view of the working end of the embodiment of FIG. 10;

FIG. 13 is a cross sectional view of the working end of the embodiment of FIG. 10;

FIG. 14 is a top view of another embodiment of the surgical instrument in its entirety;

FIG. 15 is a side view of the working end of the embodiment of FIG. 14;

FIG. 16 is a second side view of the working end of the embodiment of FIG. 14;

FIG. 17 is a top view of a working end of the embodiment of FIG. 14;

FIG. 18 is a top view of a second working end of the embodiment of FIG. 14;

FIG. 19 is a top view of another variation of the embodiment of FIG. 14;

FIG. 20 is a side view of the working end of the variation shown in FIG. 19;

FIG. 21 is a cross sectional view of the embodiment of FIG. 19;

FIG. 22 is a second cross sectional view of the embodiment of FIG. 19;

FIG. 23 is a view of a pin in its entirety;

FIG. 24 is an enlarged view of the end of the pin of FIG. 23; and

FIG. 25 depicts a hollow tube to be used in conjunction with the embodiment of FIG. 23.

DETAILED DESCRIPTION

Figure 26:
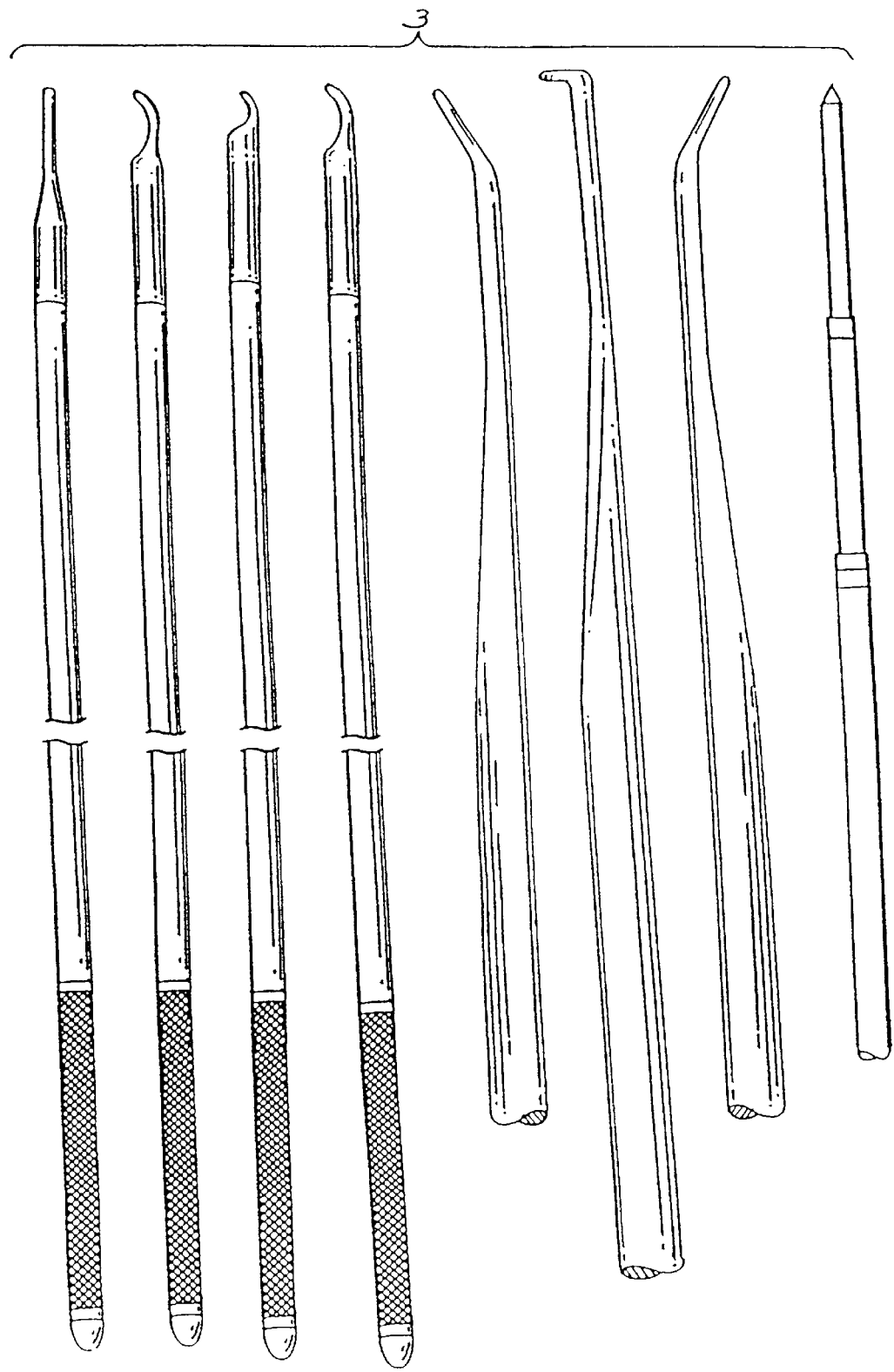
FIG. 26 depicts an embodiment of the present invention wherein a group or kit of at least some of the embodiments of the instruments of the present invention is provided for use in performing a minimally invasive surgical procedure.

The accompanying Figures depict embodiments of the surgical instruments of the present invention, and features and components thereof. With regard to means for fastening, mounting, attaching or connecting components of the present invention to form the instruments as a whole, unless specifically described otherwise, such means are intended to encompass conventional fasteners such as machine screws, machine threads, seals, snap rings, clamps, rivets, nuts and bolts, toggles, pins and the like. Components may also be connected adhesively, by soldering or friction fitting, or by welding or deformation, if appropriate. Unless specifically otherwise disclosed or taught, materials for making components of the present invention are selected from appropriate materials such as metal, metallic alloys, natural or synthetic materials, plastics and the like, and appropriate manufacturing or production methods including casting, extruding, molding and machining may be used.

Any references to front and back, right and left, top and bottom, upper and lower, and horizontal and vertical are intended for convenience of description, not to limit the present invention or its components to any one positional or spacial orientation.

A number of instrument embodiments of the invention are shown in FIGS. 1–25, and FIG. 26 depicts that a selected number of the embodiments or selected embodiments may be assembled, gathered or provided as a kit or group 3 of instruments for performing a surgical procedure, particularly a procedure such as a minimally invasive spinal procedure. In general, the instruments of the invention may be used as surgical instruments for dissection and retraction in minimally invasive, laparoscopic, or other procedures. The embodiments of the present invention are shaped to aid in dissection and retraction in minimally invasive procedures, and are well-suited for use in spinal procedures. In these procedures, the entry point for the procedure (typically through trocar ports) may vary, although it is commonly done through the abdominal incisions of various lengths. The procedure is then viewed on a monitor connected to either a camera attached to a magnifying device (such as a laparoscope or thoracoscope) which is inserted in a trocar port or through a system using X-ray or other appropriate imaging techniques. Direct visualization through a mini-incision may also be used.

a. Retractors

FIGS. 1–9 show three variations of one embodiment of the invention. FIGS. 1, 4, and 7 show a surgical instrument 10 comprising a working end 12 and a shaft 14. The working end 12 has a generally central longitudinal axis and a surface 16 generally transverse to the axis. The surface 16 has a generally toroidal shape having a concave portion 18 and a convex portion 20, as best illustrated in FIGS. 2, 5, and 8. The instrument 10, or particularly the working end 12 can be made from any variety of rigid material, such as hard plastic. Preferably, the working end 12 or a substantial portion of it, is radiolucent (i.e., partly or wholly permeable to radiation, such as X-rays) whereby it is adapted to reduce interference or to not interfere with a surgeon's ability to see other devices examined on an imaging system or displayed for viewing the surgical procedure. The working end or a portion of it may be made radiopaque for some applications.

The concave portion 18 of the surface 16 has a selected degree of openness which may vary widely. FIGS. 2, 5, and 8 show concave portions 18 of varying degrees of openness. The degree of openness of the concave portion 18 may be selected to promote ease of use of the surgical instrument 10, particularly in the manipulation of blood vessels and bodily tissue, and more particularly tissues adjacent to the spine, without harming them. The working end 12 of the embodiment of FIGS. 1–9, and particularly the surface 16, should be appropriately shaped for dissection and retraction of large blood vessels, such as the common iliac artery and vein, or similar generally tubular or cylindrical structures during surgical procedures. As can best be seen in FIGS. 2, 5, and 8, the surface 16 of the instrument 10 defined by the concave 18 and convex portions 20 defines a gently rounded, "soft" edged scoop-shaped working surface. The face 19 of the concave portion 18 of the surface 16 preferably is flat from the edge 22 on one side of the concave portion 18 to the edge 22 on the other side. In other words, a straight line may be formed along the face 19 of the concave portion 18 along an axis perpendicular to the longitudinal axis. The thickness of the surface 16, which is the distance between the concave portion 18 and the convex portion 20, may vary, as illustrated by the different embodiments in FIGS. 2, 5, and 8.

The surface 16 is also defined in that it has a smoothly rounded continuous edge 22 having a first end 24 at a shoulder 26 and a second end 28 also at the shoulder 26 and spaced from the first end 24. The edge 22 defines the working surface 16 of the invention. For instance, on one side of the edge 22 lies the concave portion 18, which is the side primarily used for manipulation of bodily tissue. The convex portion 20 is on the other side of the edge 22. The area between the concave 18 and convex portions 20 defined by the edge 22 may be either flat or rounded. The edge 22 is preferably not a sharp edge, but is preferrably blunt so that it will not harm bodily tissue during use. The shoulder 26 is a ring of slightly increased diameter around the circular area of the working end 12 just below the surface 16. The shoulder 26 defines the portion of the working end 12 where the concave 18 and convex portions 20 begin, and hence where the scoop-shaped working surface begins. The surface 16 of the invention should be smooth so that it does not harm bodily tissue when in use. Similarly, the tip 32 of the working end 12 may be rounded and blunt to prevent harm to bodily tissue.

In the embodiments of the invention shown in FIGS. 1–9, the concave 18 and convex portions 20 of the working end 12 do not extend beyond the diameter of the shaft 14. The concave 18 and convex portions 20, similarly, do not extend beyond a line parallel with the longitudinal axis along an outer diameter of the working end 12 below the shoulder 26. Because the convex portion 20 does not extend beyond the diameter of the shaft 14 or working end 12, it does not interfere with the passage of the working end 12 under the deep side of a blood vessel during use of the surgical instrument. This feature of the invention also may be important because it allows the surgical instrument 10 to be inserted in a hollow tube, port, or typical trocar (not shown in Figures) for insertion into the body cavity. A tube or sheath may be used along with the instrument 10 so that the working end 12 does not harm the tissue as it traverses the body cavity to reach the area of manipulation. The width of the surface 16 of these embodiments is determined as the functionally optimal while still fitting through a trocar port and hollow tube (approximately 11–12 millimeters in width). An increased width of the surface 16 prevents harm to blood vessels during use of the instrument 10. The width of the surface 16, therefore, may be the same as the diameter of the circular portion of the working end 12 below the surface 16 and near the shaft 14.

As shown in the Figures, particularly FIGS. 3 and 6, in one embodiment the surface 16 of the invention includes a neck portion 30 of decreased width than the remainder of the surface 16. The width of this neck portion 30 may vary so that the invention may be used in various situations to manipulate body tissue, such as segmental vessels, and the cystic duct during cholecystectomy.

The length of the working end 12 of the invention may vary. In one embodiment the working end is approximately 2 to 4 inches in length, with the surface 16 of the working end 12 approximately 1 to 2 inches in length. The shaft 14 may be of any appropriate length and should be long enough to traverse the body cavity, such that it may be inserted in one end of the body to manipulate tissue at the other end of the body cavity. In one embodiment the shaft 14 is approximately 10 to 20 inches in length. The diameter of the shaft 14 and of the working end 12 should as wide as for physician comfort and ease of use while still fitting through the desired trocar port. In one embodiment, during the use of a trocar port of 12 millimeters in diameter, the diameter of the shaft is approximately 11 millimeters so that it will fit through trocar port.

In one embodiment, the shaft 14 may be removably connected to the working end 12. As shown best in FIGS. 3, 6, and 9, the end of the working end 12 opposite the surface 16 may contain male threads 34 to mate with female threads 36 in the shaft 14. Other methods for connection known to those skilled in the art may also be used. In the depicted or a similar manner, the working end 12 is easily removable from the shaft 14 so that a small number of shafts 14 may be used with a larger number of working ends 12. Alternatively, in another embodiment, the working end 12 may be permanently joined or coupled to the shaft 14 by methods known to those skilled in the art, or the working end 12 and shaft 14 may be formed as a single piece. The end or a portion 38 of the shaft 14 opposite the working end 12 may be gnarled or textured to aid in gripping the shaft 14, and may be larger in diameter than the remainder of the shaft.

Another embodiment of the invention is shown in FIGS. 10–13. In this embodiment, the working end 12 is defined by a generally curved surface 50 along the longitudinal axis. In other words, the curvature in this embodiment is in a direction that is generally perpendicular to the curvature of the embodiment in FIGS. 1–9. The curved surface 50 has a concave portion 52 and a convex portion 54, as can best be seen in FIG. 13. The surface 50 also has a generally flat tip 56. The curvature of the surface 50 may vary. This embodiment of the surgical instrument 10 has a smooth continuous edge 58, which defines the boundaries of the working face 60 of this embodiment. This continuous edge 58 extends from the flat tip 56 along both sides of the surface 50 and meets at the outer diameter of the working end 12 at a length of approximately 1 to 2 inches from the flat tip 56. The face 60 of the invention slants gradually outward toward the outer edge 62 of the working end 12 from an initial depth at approximately the center of the working end 12 near the flat tip 56. The width of the face 60 gradually decreases with distance away from the flat tip 56.

The length of the working end 12 of this embodiment of the invention may vary. In one embodiment the working end 12 is approximately 2 to 4 inches in length, with the surface 50 of the working end 12 approximately 1 to 2 inches in length. The shaft 14 of this embodiment of the invention may have approximately the same characteristics as the embodiment shown in FIGS. 1–9 and described above. The working end 12 in this embodiment, therefore, may be permanently or removably coupled to the shaft 14.

b. Dissectors

FIGS. 14–22 show another embodiment of the invention. In this embodiment of the invention, the working end 12 has a generally longitudinal axis and a surface 70 that is generally transverse to the axis. The surface 70 may be generally spatulate and oval, as best seen in FIGS. 17 and 18, and may be set at an angle $\alpha$ relative to the axis. In one variation of this embodiment, the angle $\alpha$ is between 0 and 90 degrees. In the embodiment shown in FIGS. 15 and 16, for instance, the angle $\alpha$ is approximately 20 to 45 degrees. This embodiment may prove helpful in slipping underneath certain bodily tissue when the angle of the working end 12 relative to the shaft 14 is important in accessing certain areas, such as mid-sacral and segmental blood vessels and the cystic duct. In another variation of this embodiment, shown in FIGS. 19–22, the angle $\alpha$ is approximately 90 degrees.

The surface 70 of this embodiment may have substantially flat upper and lower surfaces 72, 74, respectively. The width 76 and thickness of the surface 70 in this embodiment is generally thin. In one embodiment, for instance, the width 76 of the surface is approximately 2 to 5 millimeters. This embodiment of the invention may be useful in slipping underneath certain bodily tissues to separate and remove it from near other tissue. More specifically, this embodiment of the invention promotes and facilitates separation (dissection) of blood vessels from often tightly adherent tissue, such as the mid sacral and segmental vessels and other types of tissue deemed appropriate by the surgeon, such as the iliolumbar vein, a branch of te left common iliac vein. This embodiment may be used for dissection of vessels, such as the cystic or uterine arteries, prior to anticipated occlusion with clips and/or suture, or coagulation with an electrocautery device.

In the embodiment of the invention shown in FIGS. 14–18, the surface 70 is offset in reference to the shaft 14. The surface 70 in this embodiment may have a continuous edge 78. with a selected degree of curvature on a first side 80 and a substantially straight second side 82 opposite the first side 80. As can best be seen in FIGS. 17 and 18, the curved first side 80 of the edge 78 causes the surface 70 to be offset from the shaft 14. The straight second side 82 does not extend beyond the width of the working end 12 or shaft 14 adjacent to the surface 70. The curved first side 80, however, may extend beyond the width of the shaft 14 or working end 12 adjacent to the surface 70. The straight side 82 of the surface 70 may be ideal for placement against some bodily tissue, while the surface 70 is slid between different tissues to separate the tissues with the curved side 80 of the surface 70. This embodiment of the invention may assist in the detachment and separation of blood vessels from adjacent attachments or from themselves. An example is their use in the separation of the left common iliac artery and vein from each other during exposure of or access to the $L_{4-5}$ disc during anterior spinal fusion. This embodiment is also helpful in the separation of the sympathetic chain from the vertebrae during laparoscopic or thoracoscopic sympathectomy. In one embodiment, the oval or spatulate-shaped surface 70 has a diameter of approximately 5 to 10 millimeters, but this size may be varied as long as its use in mini-laparotomy or other minimally invasive surgical procedures is not impaired.

Much like the other embodiments of the instruments 10 of the present invention, the working ends 12 of the embodiments of FIGS. 14–22 are connected to a shaft 14. The working ends 12 may be removably or permanently connected to shafts 14. As best illustrated in FIGS. 15, 16, and 20, the end of the shaft 14 near the working end 12 may be tapered. The taper of the shaft 14 allows for better vision of the laparoscopic field or laparoscopic image as seen on the monitor. The end of the shaft 14 opposite the working end 12 may be gnarled (the gnarls are represented by numeral 38 in FIG. 14) for grip. The diameter of the shaft 14 in this embodiment may generally vary, as long as it is convenient for use in minimally invasive surgical procedures.

c. Pins for Retraction

FIGS. 23 and 24 show another embodiment of the invention. This embodiment is a straight, substantially rigid pin 90 for being placed into hard tissue. The pin 90 has a sharp tip 92 and a number of steps 94 generally adjacent to the tip 92. The pin 90 increases incrementally in diameter with each step 94, and may be of a generally round shape. The pin 90 may also have etched or superficial marks 96 provided along the length of the pin 90. The etched marks 96 in the embodiment shown in FIG. 24 are in the region of the steps 94 and are approximately 1 cm apart. The diameter of the pin 90 may vary; in one embodiment it is approximately ¹⁄₃₂ of an inch near the tip 92, increasing to approximately ³⁄₃₂ or ⅛ of an inch near the outer steps 94 of the pin 90. The diameter of the pin 90 should be chosen to allow for hammering of the pin 90 into the bone without bending. The end of the pin 90 opposite the sharp tip 92 contains a blunt tip 98 that is ideal for hammering. A portion of the blunt tip 98 may also contain gnarls to aid the surgeon in gripping and manipulating the pin 90.

In practice, the pin 90 is hammered into bone so that it holds a blood vessel or other tissue in a selected place during a surgical procedure. The pin 90 may be used in minimally invasive or other surgical procedures. The pin 90 may be used to mark specific bones or depths of bones (such as specific intervertebral disc levels) during surgery. The etched marks 96 and the steps 94 serve multiple purposes. The steps 94 serve to inform the surgeon as to the depth of penetration of the pin 90 into the bone. The steps 94 also provide a positive stop to prevent inadvertent passage or hammering of the pin 90 deeper into the bone than is desired. The etched marks 96, similarly, serve to denote the depth of the pin 90 from the tip 92 into the bone. In one embodiment, the etched marks 96 are spaced at 1 centimeter and 2 centimeter depths from the tip 92. The surgeon, therefore, may easily determine the depth of the pin 90 into the bone so that the surgeon does not inadvertently damage the bone or spinal cord of the patient. In one embodiment, the pin 90 is at least 10 to 12 inches long so that it is long enough to traverse the diameter of the body cavity while in use.

FIG. 25 shows a hollow tube 100 to be used in connection with the pin 90. The tube 100 is shorter than the pin 90. In one embodiment, the tube is approximately 1 to 3 inches shorter than the pin 90, but this length relationship may be varied as long as the tip is able to be retracted into the tube and as long as it may be driven into a selected bone without interference. In this embodiment, therefore, the tube 100 may be approximately 12 to 14 inches in length. The purpose of the tube is to contain the sharp tip 92 of the pin 90 during its passage through the abdominal or thoracic cavity (or other body cavity) during surgery. The diameter of the tube 100 should be slightly greater than that of the pin 90. The tube 100 may also contain a locking mechanism 102 to lock the pin 90 in place within the tube 100 to prevent it from falling out of the tube and into the patient's body. The locking mechanism 102 shown in FIG. 25 is a simple screw, although any other type of locking mechanism 102 known to those skilled in the art may be used. The ends of the tube may be blunt, so that the body is not harmed by the tube, and the ends may also contain slight bevels 104.

In practice, the locking mechanisms 102 are tightened during transfer of the pin 90 through the body cavity to where it will be hammered into the bone. Once there, the lock is loosened, and the pin 90 is advanced and hammered into place. If the tube 100 is longer than the pin 90, the connection between the tube 100 and the pin 90 may be tightened and the tube 100 may then be hammered into place. Once in place, the guide tube may rest against the bone into which the pin 90 was hammered, remaining as a pin sheath during the surgery. At the conclusion of the surgical procedure, the pin 90 is withdrawn so that the tip 92 lies within the tube 100, the locking mechanisms 102 are tightened around the pin 90 so that the tip 92 is within the tube 102, and then the pin 90 and guide tube 102 are withdrawn.

While the present invention has been described with reference to several embodiments thereof, those skilled in the art will recognize various changes that may be made without departing from the spirit and scope of the claimed invention. Accordingly, this invention is not limited to what is shown in the drawings and described in the specification but only as indicated in the appended claims.

What is claimed is:

1. A set of surgical instruments for use in surgical procedures, comprising:
   (a) at least one or more retractors; and
   (b) at least one or more dissectors; and
   (c) at least one or more pins; and
   (d) wherein the set of surgical instruments is sterilized and in packaging.

* * * * *